United States Patent [19]

Giaever

[11] 4,018,886
[45] Apr. 19, 1977

[54] DIAGNOSTIC METHOD AND DEVICE EMPLOYING PROTEIN-COATED MAGNETIC PARTICLES

[75] Inventor: Ivar Giaever, Schenectady, N.Y.

[73] Assignee: General Electric Company, Schenectady, N.Y.

[22] Filed: July 1, 1975

[21] Appl. No.: 592,196

[52] U.S. Cl. .................. 424/12; 23/230 B; 23/253 R; 23/259; 128/2 R; 210/222; 260/112 R

[51] Int. Cl.² .............. G01N 21/46; G01N 27/00; G01N 31/06; G01N 33/16

[58] Field of Search ........... 23/230 B, 253 R, 259; 424/12; 210/222

[56] References Cited

UNITED STATES PATENTS

| | | | |
|---|---|---|---|
| 2,666,355 | 1/1954 | Trurnit | 424/12 X |
| 3,470,067 | 9/1969 | Warren | 210/222 X |
| 3,539,509 | 11/1970 | Heitmann | 210/222 X |
| 3,657,119 | 4/1972 | Turbeville | 210/222 X |
| 3,843,324 | 10/1974 | Edelman | 424/12 X |
| 3,933,997 | 1/1976 | Hersh | 23/230 B |

Primary Examiner—Sidney Marantz
Attorney, Agent, or Firm—Leo I. MaLossi; Joseph T. Cohen; Jerome C. Squillaro

[57] ABSTRACT

Small magnetic particles are used to provide large and widely-distributed surface area for separating a select protein from a solution to enable detection thereof when present in low concentrations. The particles are coated with a protein that will interact specifically with the select protein.

15 Claims, 3 Drawing Figures

DIAGNOSTIC METHOD AND DEVICE EMPLOYING PROTEIN-COATED MAGNETIC PARTICLES

BACKGROUND OF THE INVENTION

This invention relates to the detection of proteins by the utilization of the phenomenon by which such proteins interact specifically either immunologically or nonimmunologically.

Constructions of diagnostic devices for use in the immunological detection of proteins as well as methods and apparatus for the purification of proteins are disclosed in the related copending U.S. applications of Giaever, Ser. No. 266,278, filed June 26, 1972, now abandoned, and Ser. No. 384,113, filed July 30, 1973, now abandoned. Other constructions of diagnostic devices for use in the immunological detection of biological particles are disclosed in the related copending U.S. applications of Giaever, Ser. No. 445,204, filed February 25, 1974, now U.S. Pat. No. 3,926,564, and Ser No. 580,603, filed May 27, 1975, now U.S. Pat. No. 3,979,184. An improved diagnostic method for determing the presence or absence of select biological particles by the utilization of "tagging" (e.g. radioactive isotopes) and a cleaving operation is disclosed in copending U.S. patent application Ser. No. 573,610 — Giaever, filed May 1, 1975.

Method and apparatus specific for the detection of viruses, bacteria and other cells is disclosed in U.S. Pat. No. 3,853,467 — Giaever.

This application is related to concurrently filed U.S. patent application Ser. No. 592,195 — Giaever entitled "Magnetic Separation of Cells" commonly assigned and filed July 1, 1975, now U.S. Pat. No. 3,970,518.

DESCRIPTION OF THE INVENTION

The diagnostic method according to this invention for determining the presence or absence of select proteins in low concentration in a liquid sample comprises the steps of applying to the surface of small magnetic particles a coating of protein specific to the select protein; moving these protein coated magnetic particles through the liquid sample whereby the particles become coated with a second protein layer, the second layer being the select protein; separating the double layer-coated magnetic particles from the liquid sample; introducing the double layer-coated magentic particles into a solution of cleaving agent in contact with a metallized surface whereby the bonds between the specific protein and the select protein are broken permitting the select protein to diffuse to the metallized surface, and inspecting the metallized surface for the presence of adsorbed protein.

BRIEF DESCRIPTION OF THE DRAWING

The subject matter of the instant invention for which protection is sought is presented as claims at the conclusion of the written description of the invention set forth herein. The description sets forth the manner and process of making and using the invention and the accompanying drawing forms part of the description schematically illustrating one embodiment. The views include:

MANNER AND PROCESS OF MAKING AND USING THE INVENTION

As used herein, the term "metallized surface" encompasses both metallic surface area and metallic surface area containing oxide of one or more metals present.

The apparatus disclosed herein is merely exemplary and, after an understanding of the method of this invention, other embodiments may be readily devised.

Reaction vessel 11 made of non-magnetic material, for example, glass, plastic, stainless steel, is used for the conduct of certain mixing and separation steps according to this invention.

Figure 1:
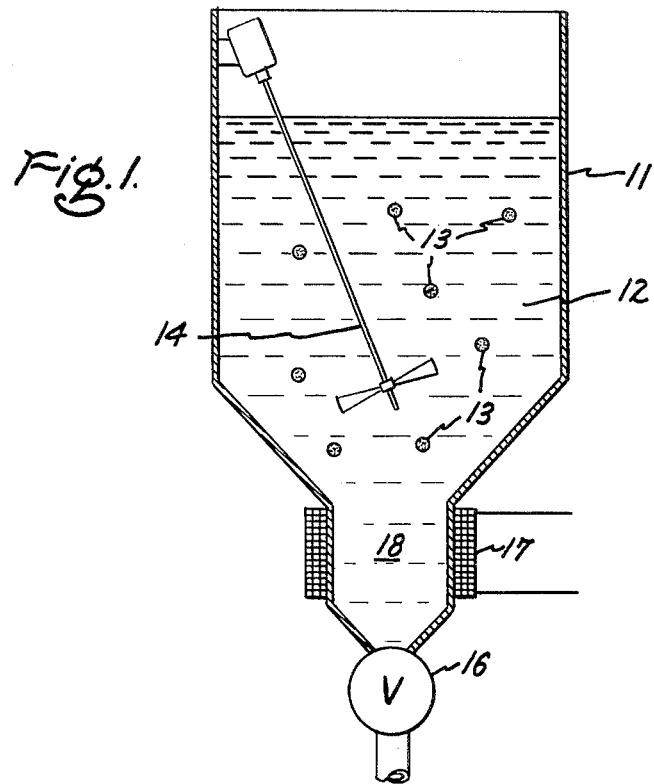
FIG. 1 showing a section through apparatus that may be employed for the distribution of small magnetic particles in a liquid and subsequent separation of the particles from the liquid.

As shown in FIG. 1, vessel 11 contains a fluid together with initially uncoated solid particles 13 in suspension therein. Numeral 12 broadly refers to the different liquids employed at stages of the method. Agitating means 14 is employed to cause the movement of particles 13 through liquid 12 for the purpose described hereinbelow. Particles 13 are magnetic and range in size from colloidal to about 10 microns. Ferromagnetic, ferrimagnetic and superparamagnetic materials are useful in the practice of this invention. Other suitable magnetic materials include oxides, such as, for example, ferrites, perovskites, chromites and magnetoplumites.

Initially, the liquid 12 would be a liquid containing a significant concentration of a protein specific to the select protein to be detected and the small magnetic particles 13 are dispersed and stirred therethrough as noted above. Thus, in a relatively short time, the surfaces of particles 13 become coated with a monomolecular layer of specific protein present in liquid 12. It is not necessary that a solution of pure specific protein be employed as long as a significant fraction of particles 13 become coated with the correct (specific) protein.

Once the monomolecular layer has been produced the coated magnetic particles 13 are separated from liquid 12. This separation is accomplished by the provision of a magnetic field of sufficient strength to hold back magnetic particles 13, when valve 16 is opened permitting the liquid to leave vessel 11. The requisite magnetic field is provided by coil 17, which may be selectively energized to capture the magnetic particles as an electromagnet. Particles 13 so immobilized may be retained for washing thereof in region 18, if desired, after the drainage of the liquid from vessel 11.

Next, it is merely necessary to reintroduce into vessel 11 a sample liquid (e.g. blood) suspected of containing the select protein. Valve 16 will have previously been closed and coil 17 deactivated whereby particles 13 will be free to be moved through this new liquid (still designated 12) by means of agitator 14 so that in a very short time the magnetic particles 13 coated with a monomolecular layer of the protein specific to the select protein will collect all of the select protein available in the sample liquid as a second monomolecular layer by the specific complexing interaction between these proteins.

This positive circulation of the magnetic particles coated with the specific protein eliminates the long diffusion time that normally would be required for antibodies (antigen) to reach some given surface for conduct of the immunologic reaction with a layer of antigen (antibodies) disposed on that surface.

Once the available select protein has been collected from the sample liquid, the coated magnetic particles are easily separated from the sample fluid as described above by activating coil 17 and opening valve 16 whereby the liquid is released and the magnetic particles are held back. Washing of the coated magnetic particles follows to remove nonspecific reactions. The washing may be accomplished either by continuing to hold the magnetic particles under the influence of the magnetic field from coil 17 while pouring wash liquid (e.g. distilled water or dilute aqueous salt solution) into reactor 11 to pass through the collection of magnetic particles and out via valve 16 or, if desired, by closing valve 16, deactivating coil 17, introducing wash liquid into reactor 11, applying gently agitation via agitator 14 and then separating the coated magnetic particles from the wash liquid in the manner described hereinabove in previous separations.

Figure 2:
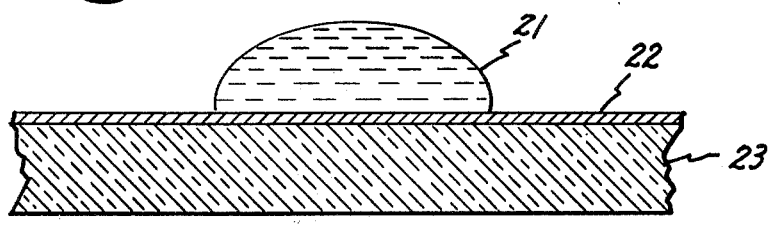
FIG. 2 shows in cross-section a diagnostic substrate having cleaving agent disposed in contact with the metallized surface thereof and FIG. 3 shows in cross-section the distribution of select protein over the metallized surface after the cleaving action has been accomplished.
Figure 3:
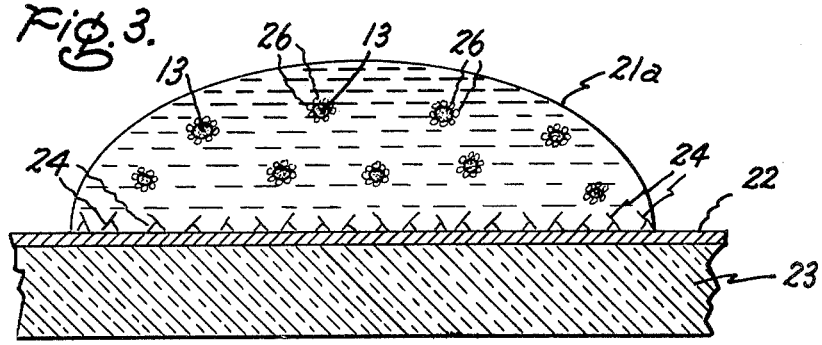

Next, any of the diagnostic devices described hereinabove in the aforementioned Giaever patent applications or other substrates presenting a metallized surface may be selected for detection of the select protein in the following manner. A drop 21 of cleaving agent solution such as a weak acid solution, alkaline solution or a solution containing a concentration of salt is placed upon metallized surface 22, which may, for example, be bonded to a substrate 23. Substrate 23 as illustrated in FIGS. 2 and 3 is made of glass, but the substrate employed is a matter of choice. A 0.1 normal (N) citric acid solution is preferred for the purposes herein described. The range of concentrations of the citric acid that may be used for obtaining the desired results are approximately 0.01 to 1.0 N.

The cleaving agent must be sufficiently strong to break the bond between the second (select) and first (specific) monomolecular protein layers coating magnetic particles 13, but not strong enough to cleave, or otherwise affect, the bond between the first (specific) monomolcular layer of protein and the solid surface of any given magnetic particle 13 to which it is adsorbed. Other suitable weak acids that may be utilized are 0.1 N malic acid and 0.1 N formic acid. Stronger acids such as hydrochloric acid and sulfuric acid may also be utilized but in a much smaller concentration (i.e. approximately 0.01 N). In the case of an acid cleaving agent preferably the pH is the range between 2 and 5, although a pH as low as 1.0 has been satisfactorily utilized with 0.1 N hydrochloric acid.

With respect to alkaline and high salt concentration solutions used as cleaving agents, the alkaline solution useful herein would have a pH in the range 9–13, and typically, a 0.2 N sodium hydroxide solution has been used. Various salt solutions of elevated salt concentration, such as NaCl and NaI are known to function as cleaving agents.

Washed bi-molecular coated magnetic particles 13 are introduced into drop 21 of citric acid. The drop containing the magnetic particles is designated 21a. The citric acid breaks the bonds between the select protein and the specific protein (antigen-antibody bonds) whereupon the specific protein molecules 24 diffuse to the metallized surface 22 and become adsorbed thereon. The molecules 26 of the specific protein remain adsorbed on the magnetic particles 13.

A convenient way to introduce the bi-molecular layer-coated magnetic particles 13 into drop 21 is by removing particles 13 from reactor 11, adding a small amount of distilled water thereto, thereafter, transferring a drop of the highly concentrated suspension of magnetic particles to merge with drop 21 forming the larger drop indicated by the numeral 21a.

After a period of incubation of 1 hour the metallized surface is washed and then inspected for the presence of a layer of the adsorbed protein molecules 24 either visually or by the use of an ellipsometer. The presence of adsorbed protein on metallized surface 22 establishes the presence of molecules of the select protein in the sample liquid.

EXAMPLE

Nickel particles about 1 micron in diameter were coated with bovine serum albumin (BSA). The coating period was 5 minutes and the concentration of the BAS was 100 micrograms per milliliter. The BSA-coated nickel particles were introduced into human serum containing antibodies to BSA (rabbit anti-serum BSA obtained from Miles Laboratory). The antibody concentration was 1 microgram/ml and the incubation period was 10 minutes. After washing, the bi-molecular layers on the nickel particles were cleaved in a drop of 3 molar solution ammonium thiocyanate on an indium-coated glass slide. Presence of the resulting monomolecular layers on the surface of the slide was visually discernible.

The particular apparatus disclosed in FIG. 1 is merely exemplary and other arrangements may be readily employed to carry out the method disclosed and claimed herein and constituting the best mode contemplated. The stirring of magnetic particles 13 may, for example, be accomplished by the use of a magnetic coil. The sequence of liquids employed may be maintained in separate compartments in a multi-compartment unit disposed within such a magnetic coil and a second magnet may be employed to effectuate the transfer of magnetic particles 13 for the conduct of this process. Preferably, the magnetic particles already coated with some given specific protein would be made available commercially for carrying on diagnosis for the presence of some select protein.

What I claim as new and desire to secure by Letters Patent of the United States is:

1. A diagnostic method for determining the presence or absence of select protein in a liquid sample comprising the steps of:
   dispersing a plurality of finely-divided magnetic particles each of which is coated with a layer directly bonded thereto of first protein molecules specific to said select protein in the sample liquid to facilitate contact between said coated particles and said sample liquid;
   magnetically retrieving and separating said coated particles from said sample liquid;
   washing said coated particles;
   introducing said coated particles into a volume of cleaving agent solution in direct contact with a metallized surface to permit select protein, if present, to detach from the first protein-coated particles and
   examining said metallized surface for the presence of protein adsorbed thereon.

2. The diagnostic method recited in claim 1 wherein the magnetic particles are selected from the group consisting of ferromagnetic and ferrimagnetic materials.

3. The diagnostic method recited in claim 1 wherein the examining step is accomplished by the use of an ellipsometer.

4. The diagnostic method recited in claim 1 wherein the magnetic particles are held by means of an electrically induced magnetic field during the washing step.

5. The diagnostic method recited in claim 1 wherein the dispersing of the magnetic particles is accomplished magnetically.

6. The diagnostic method recited in claim 1 wherein the metallized surface is substantially planar.

7. The diagnostic method recited in claim 1 wherein the metallized surface is non-planar.

8. The diagnostic method recited in claim 1 wherein the specific protein is antigen and the select protein is antibody thereto.

9. The diagnositc method recited in claim 1 wherein the select protein is antigen and the specific protein is antibody thereto.

10. The diagnositc method recited in claim 1 wherein the cleaving agent solution is a weak acid solution.

11. The diagnostic method recited in claim 10 wherein the pH of the acid solution is in the range of 1–5.

12. The diagnostic method rectied in claim 10 wherein the acid is citric acid.

13. A diagnostic device for determining the presence or absence of select protein in a liquid sample comprising in combination a plurality of finely divided magnetic particles, surface area of which is coated with antibodies directly bonded thereto, said antibodies being specific to said select protein.

14. The diagnostic device of claim 13 wherein the magnetic particles are in the size range of from about colloidal size to about 10 microns.

15. The diagnostic device of claim 13 wherein the magnetic particles are made of nickel.

* * * * *